United States Patent [19]

Jette

[11] 4,134,684

[45] Jan. 16, 1979

[54] REPEAT DEFECT DETECTOR SYSTEM

[75] Inventor: Paul C. Jette, Bethel, Conn.

[73] Assignee: Intex Corp., Norwalk, Conn.

[21] Appl. No.: 760,279

[22] Filed: Jan. 18, 1977

[51] Int. Cl.² ..................... G01N 21/32; G01N 21/16
[52] U.S. Cl. ..................................... 356/430; 250/563
[58] Field of Search ............... 356/200, 199, 209, 212; 250/563, 572

[56] References Cited
U.S. PATENT DOCUMENTS

| | | | |
|---|---|---|---|
| 3,781,117 | 12/1973 | Laycak et al. | 250/563 |
| 3,898,469 | 8/1975 | Nichols et al. | 250/563 |
| 3,958,127 | 5/1976 | Faulhaber et al. | 250/563 |
| 3,980,891 | 9/1976 | Slaker | 356/200 X |

*Primary Examiner*—Vincent P. McGraw
*Assistant Examiner*—Rodney B. Bovernick

*Attorney, Agent, or Firm*—Levinson, Joseph

[57] ABSTRACT

A flaw detection system is provided in which a source of radiation is scanned across a web of moving material being examined for repeat defects. The web is divided into lanes for processing purposes, and flaw information derived from the surface of material being examined is processed to provide a two-coordinate matrix location (lane and down-web), which is stored. This circuitry without the matrix outputs has other applications. Separation distances of a repeat flaw in the same lane are compared with a predetermined list, and if a match occurs, future flaw locations are projected in that lane. A repetition of a predetermined number of flaw repeats in a given lane signals an alarm. A predetermined number of misses in a row will result in the clearing of that lane of the particular flaw that failed to repeat.

7 Claims, 4 Drawing Figures

REPEAT DEFECT DETECTOR SYSTEM

BACKGROUND OF THE INVENTION

This invention relates to a flaw detection system for the detection of defects on a moving web or sheet of material, and more particularly to a method and apparatus for such a system which provides a repeat defect detection system. A more general purpose circuit is incorporated which has general application to other systems in the automatic inspection field.

In U.S. Pats. Nos. 3,900,265 and 3,980,891, which are assigned to the assignee of the present invention, flaws or defects are detected on the surface of the material being examined by repeatedly scanning a source of radiation, such as a laser beam, across the surface of a moving web or sheet of material. The laser light is reflected, transmitted, or scattered from the material being examined, depending on the characteristics of that material, which light is picked up by a receiver having a suitable detector such as a photomultiplier tube. At any instant of time during the scan the photomultiplier output varies with the reflectivity, transmissivity, or scattering properties of the spot of light on the material upon which the laser beam is impinging. Deviations in the amount of light or radiation coming from the material being examined from what would be considered normal for such a material provide a means for indicating flaws or defects on the material. In U.S. Pat. No. 3,980,891, a system is provided to readily determine on what portion of the sheet of moving material the flaws occur by dividing the web of material into strips or lanes and counting the flaws and processing the flaw information with respect to the number of flaws occurring on a certain lane, strip or segment of the sheet. This has been referred to as a data-routing function. Such systems have proved excellent for a number of applications. However, for certain applications where it is desirable to detect and identify a given flaw which repeats itself on predetermined travel distances on the web of material under examination, and which discriminates against random flaws caused by noise or other inconsistencies, more sophisticated processing techniques and methods are required. For example, suppose that the web of material being examined passes over a conveyor system using a plurality of rollers having different circumferences positioned at various locations along the path of travel of the web of material. If one of the rollers accumulates some dirt or foreign matter, the chances are this will provide a flaw on the surface of the material, such as photographic film, and the flaw will repeat on the material on each complete revolution of the roller. By identifying such a repetitive flaw after a predetermined amount of travel of the web of material, the system could be shut down and the roller cleaned at the precise point where the problem has been identified, thus eliminating the problem without having to shut down and clean the entire system.

OBJECTS AND SUMMARY OF THE INVENTION

Accordingly, it is an object of this invention to provide a new and improved method and apparatus for providing a repeat defect detection capability for a flaw detection system.

A further object of this invention is to provide a new and improved repeat defect detection system for detecting repetitive flaws on predetermined areas of a moving web of material which greatly simplifies the data handling hardware to provide this capability.

Still another object of this invention is to provide a new method and apparatus for a repeat flaw detection system which eliminates errors and overload conditions generated by high data rates caused by random defects or other conditions which are not desired to be measured.

A further object of this invention is to provide a novel processing circuit which is useful in other automatic inspection systems.

In carrying out this invention in one illustrative embodiment thereof, a moving web of material which is scanned by a source of radiation for detecting flaws on the material is divided into lanes for signal processing purposes. Flaw signals generated by the system and signals generated by the lane means are applied to a settable recirculating process means to provide coordinate outputs indicative of lane number versus down-web position of each new flaw passed by the discriminator means, while locking out individual lanes with a predetermined high data rate until such predetermined high data rate disappears for a predetermined web travel. The settable recirculating process means can be used in other systems as a quantizer and rate limiter or for other purposes such as a correlator and length discriminator. Means are provided for determining separation distances between the prior flaw signals and succeeding flaw signals in a given lane, which are compared with a predetermined list of separation distances for providing matched pairs of flaws. When a matched pair of flaws is recognized, means are provided for projecting future flaw locations in that lane, which are again compared with a new flaw in that lane. After a predetermined repetition of new flaws in that lane which match projections of future flaw locations, an alarm is provided which gives an indication of the lane and repeat size of the repetitive flaws. Means are also provided for discontinuing the projections of defect locations after a predetermined number of misses occur.

DESCRIPTION OF THE PREFERRED EMBODIMENTS

The scanning system utilized in the present invention is shown and described in U.S. Pat. No. 3,980,891, but it is understood that other scanning systems may be utilized as long as they provide all of the data which is necessary in the processing and detection of repetitive flaws in accordance with the present invention.

Figure 1:
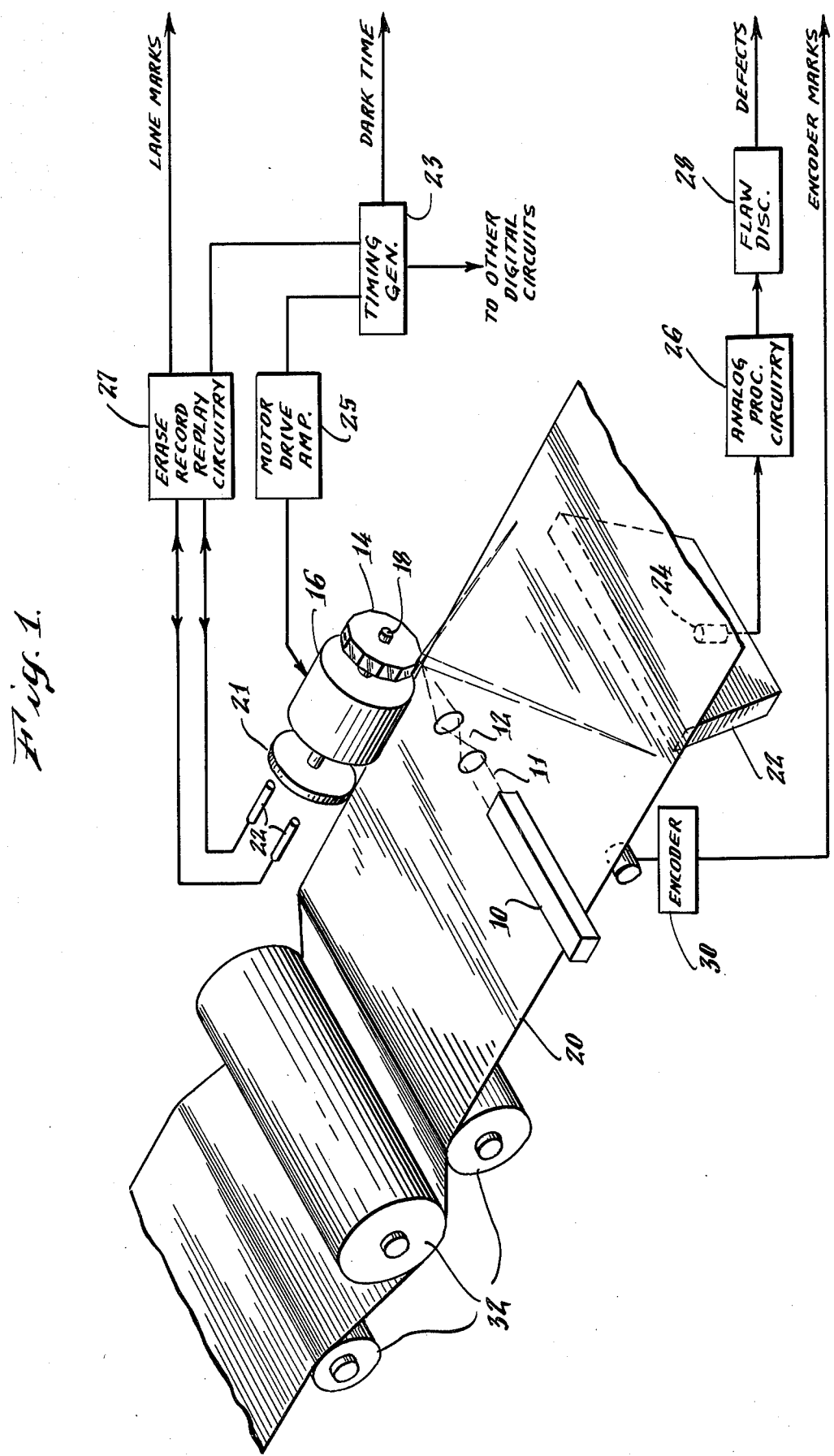
FIG. 1 is a diagrammatic representation of one type of flaw detection system which may be utilized in the present invention, with the circuitry generating the data to be processed presented in block form.

Referring now to FIG. 1, the light beam 11 generated by a laser 10 is applied by spot-forming optics 12 to a rotary scanner 14. The scanner 14 is a conventional multi-facet mirror surface polygon which is driven by motor 16 via a motor shaft 18. Motor 16 is driven by a motor-drive amplifier 25 which is coupled to a timing generator 23. The rotary scanner 14 performs the function of successively scanning the laser beam 11 across a web or sheet of moving material 20. The scanning action of the rotary scanner 14 across the material, coupled with the movement of the material, creates a raster which covers the entire area of the material as it moves under the scanner. Light transmitted through the material 20 is applied to a receiver 22 having a suitable detector 24, such as a photomultiplier therein, which detects the light applied thereto. At any instant of time during the scan, the detector 24 provides an output which is proportional to the transmission of the spot of light on the material 20 on which the laser beam 11 is impinging. Flaws occurring on the surface of the material being examined change the output of the detector 24 due to the transmissive properties of the material, thus providing a means for indicating flaws on the surface of the material. Although a transmission type system is illustrated, a reflective system where the output of the detector 24 is proportional to the reflectivity of the spot on which the laser beam is impinging is also applicable to the present invention. Different types of systems, such as reflective or transmissive, and different types of receivers may be employed in the present invention, some of which are shown and described in U.S. Pat. No. 3,900,265 cited above.

Signals from the detector are applied to analog processing circuitry 26 and from there to a flaw discriminator 28 which produces a flaw or defect output signal in accordance with the requirements of the flaw discriminator. The flaw discriminator 28 may operate on a predetermined amplitude or on differing characteristics, such as different polarities, widths, lengths, etc.

In order to provide cross-web position information with respect to where the flaw occurs on the surface of the material 20, a magnetic disc 21 is mounted on a common shaft 18 of the motor 16, and accordingly is driven synchronously with the rotating scanner 14. Lane marks recorded on the magnetic disc 21 by magnetic heads 22 are read from the magnetic disc 21 by the magnetic heads 22 and applied through the erase-record-replay circuitry 27 to provide lane marks. The lane marks may be provided on the magnetic disc 21 in accordance with the manner set forth in U.S. Pat. No. 3,980,891, or by any other suitable means as long as a means is provided by the system for feeding lane marks which represent the division of the moving web 20 into discrete strips or lanes. The web of moving material 20 may be divided into any number of lanes, the idea being to increase the signal-to-noise ratio in the processing circuitry. For purposes of illustration, the web may be divided into 128 lanes. The timing generator 23, which is also connected to the erase-record-replay circuitry 27, provides an output referred to as the "dark time," which is that period of time when the laser beam is off the web and accordingly not scanning the web.

The web of moving material is conveyed past the rotary scanner 14 by a series of rollers 32 which are spaced at different positions along the web, and the rollers have different sizes. The circumferences of the rollers are important in the processing technique, which will be explained hereinafter. As the web of moving material 20 is conveyed by the rollers 32 past the rotary scanner 14, if one of the rollers has a spot on it which marks the web of material 20, this will produce a flaw. Such a spot will recur periodically on the web, spaced at intervals corresponding to one full rotation of the given roller. Thus, by knowing the circumference of the roller, a key is provided for recognizing repetitive defects caused by a given roller.

An encoder 30 is positioned along the path of travel of the web of moving material 20 and provides encoder marks which, in effect, measure the distance the web has travelled.

Figure 2:
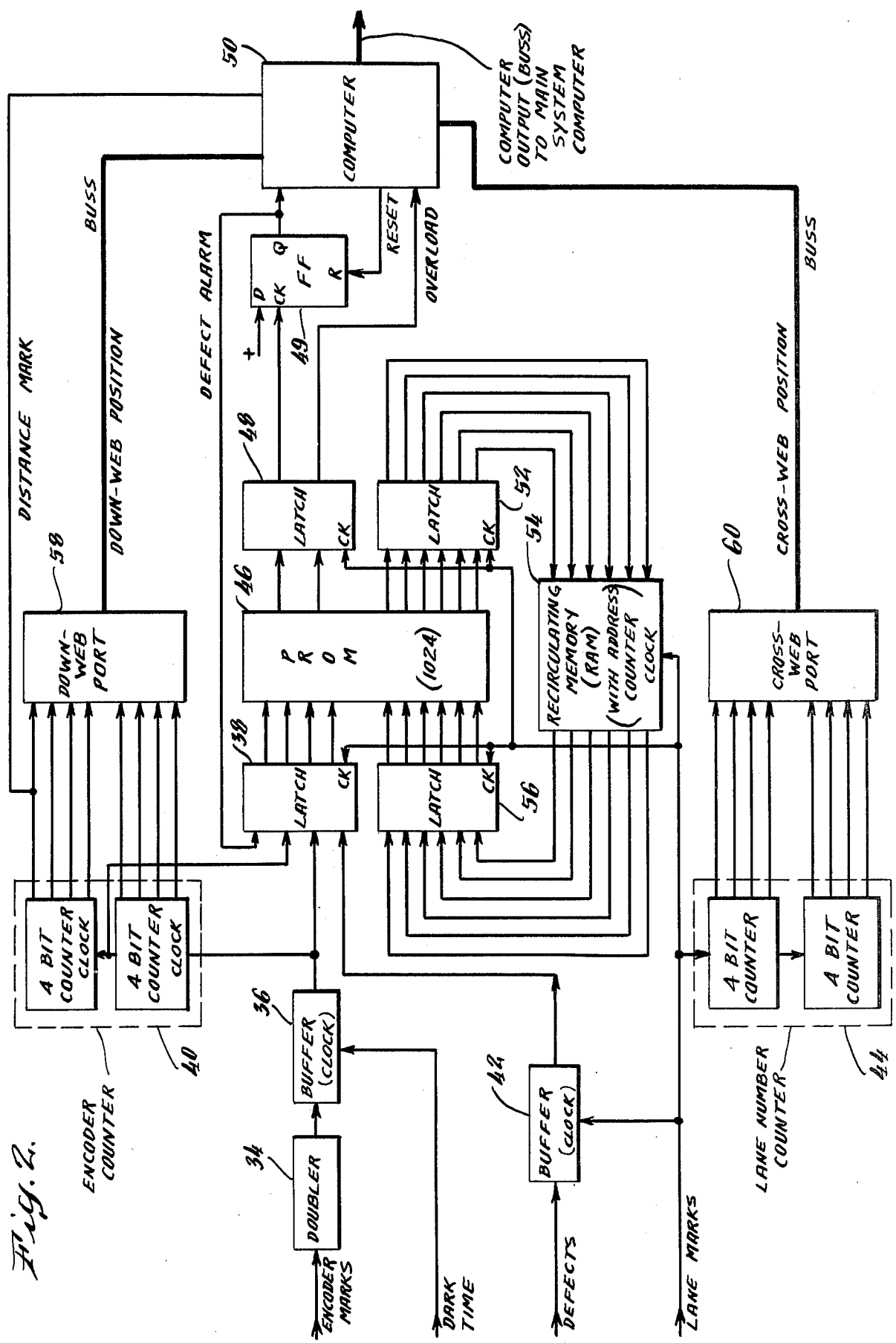
FIG. 2 is a block diagram of a data processing system used to process the data provided from the flaw detection system shown in FIG. 1.

Referring now to FIG. 2, there is shown a block diagram of front end hardware and a computer which, combined with the structure of FIG. 1, illustrates one form of the repeat defect detector embodied in the present invention. The purpose of the front end hardware is to provide the computer with matrix coordinates, namely lane number or crossweb position versus down-web position of each new defect passed by the flaw discriminator 28. Encoder marks from the encoder 30, for example, representing 0.05" of travel of the web of material 20, are applied to a doubler 34 for providing marks which, in the given example, would then be converted to 0.025" of travel. The doubler 34 is coupled to a buffer 36 which also has dark-time information supplied from the timing generator 23. The purpose of the buffer 36 is to provide a digital signal that exists for the duration of a complete scan line. The output of the buffer 36 is applied to a latch 38 and an encoder counter 40. At the same time, defects derived from the defect discriminator 28 are applied to a buffer 42 which also has applied thereto lane marks provided by the erase-record-replay circuitry 27. The buffer 42 is a signal conditioning amplifier which digitizes the signal by lane and applies it to the latch 38 for the duration of one lane. Lane marks are also supplied to a lane number counter 44. Latch 38 is coupled to a programmable read-only memory (PROM) 46 which has one set of outputs coupled to a latch 48, which is coupled through a flipflop 49 to a computer 50. The PROM 46 also has a set of outputs coupled to a latch 52 which is in turn coupled to a recirculating memory (RAM) 54, which in turn is coupled through a latch 56 back to the PROM 46. The RAM 54 may be in the form of a shift register or its equivalent, which will accommodate a variable number of lanes. PROM 46, latch 52, RAM 54, and latch 56 are intercoupled by six data channels, one of which is used for quantizing, or counting the number of discrete flaws, while five bits are used for data lockout counter purposes. The encoder counter 40 has one output representing a distance of travel mark applied to the computer 50, and with all of its outputs coupled to a down-web port 58 which has a down-web position output coupled to the computer 50. The lane number counter 44 is coupled to a cross-web port 60 whose output provides cross-web information to the computer 50.

When a defect first occurs from the flaw discriminator 28, it is applied to the latch 38 and through the PROM 46 to the latch 48, to the flipflop 49, and produces an alarm which tells the computer 50 to pick off down-web position information from the port 58 and cross-web position information from the port 60, which information is to be further processed. Further scanning of the same defect will not produce additional alarms, due to the fact that the history of that defect is sent back through the recirculating memory 54 on subsequent scans indicating the presence of that defect. If that defect disappears, its history disappears and the system is enabled for new alarms in the same lane. This quantizing of the flaws provides one and only one alarm per defect to restrict the data which must be further processed.

In the event of a whole series of defects in any given lane, high data rate lockout is provided to prevent overloading the computer with non-useful information since each defect would cause an alarm. The lockout function is performed by elements 40, 38, 46, 52, 54 and 56. These elements configure a 5-bit binary counter which counts up in the condition of a defect being fed from buffer 42, and also in the condition of an output from buffer 36 which represents the predetermined travel of the web, e.g. 0.025 inches. The counter so configured also performs the function of counting down in the absence of flaw signals from buffer 42 and in the presence of a predetermined travel of, for example, a 0.4 inch travel mark from encoder counter 40. In the illustrated embodiment the counter cannot exceed a maximum count of 31 or a minimum of zero. Alarms are disabled in that lane if the count is 24 or greater.

The circuit containing the PROM 46 and the recirculating memory 54 (e.g. a shift register, a RAM with an address counter, etc.) can be used in any type of inspection system which requires quantizing and defect rate limitation. In addition, this type of circuit can be used in other applications requiring length discrimination, down-web autocorrelation, etc.

This processing continues and if, for example, the cross-web has 128 lanes, defects are processed in the above manner for the 128 lanes, with the computer continually picking off the matrix coordinates of those lanes still enabled. All of these defects which are identified and fed to the computer are then processed in the manner to be described hereinafter in order to define a repeat defect in accordance with the system's requirements.

Figure 3:
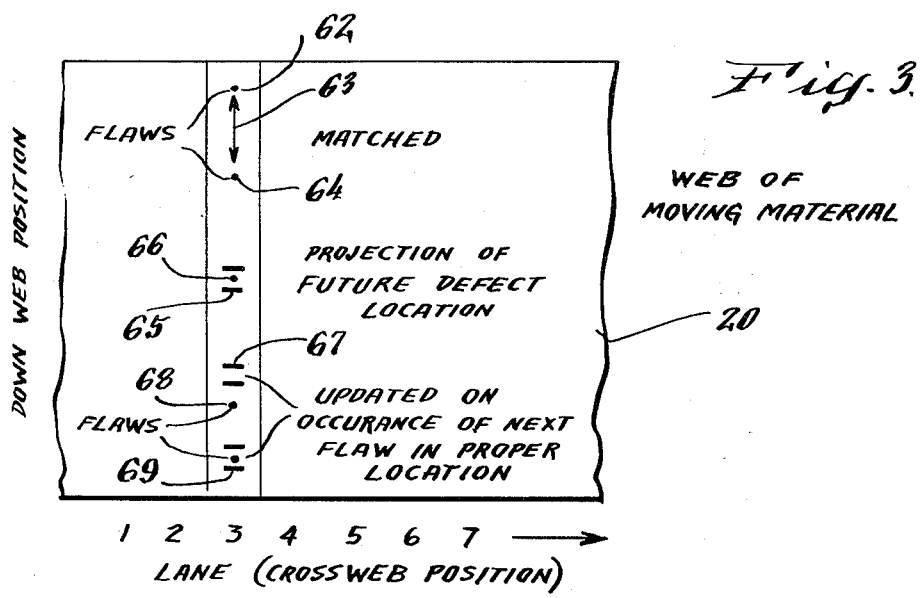
FIG. 3 shows a partial view of the web of material under examination by the scanning flaw detection system of FIG. 1 which is useful in illustrating the type of processing which is accomplished by the circuitry shown in FIG. 2.

Having the two-coordinate matrix location from the front end hardware, the remaining processing is done by the computer 50 which may be any type of general purpose computer for performing this function. Referring now to FIG. 3, the process will be explained by reference to flaws occurring in a single lane. It will be appreciated that the same type of processing is taking place in the computer 50 for the number of lanes into which the web 20 has been divided. In FIG. 3 the web of moving material 20 is partially shown with downweb position versus lane information, and flaw information is indicated only on lane 3 for purposes of illustration, it being appreciated that the same processing is taking place if and when flaws occur in the remaining lanes across the web of material 20. Upon the occurrence of the first flaw 62 occurring in lane 3, the flaw position is stored in the computer in what will be referred to as a pre-filter section of the computer 50. When the next succeeding flaw 64 occurs in lane 3, flaws 62 and 64 are separated by a down-web position distance 63. This separation distance 63 is compared with a predetermined list of repeat defect sizes. This list of repeat defect sizes corresponds to the circumferences of the rollers 32. For example, if a roller becomes contaminated in one spot and produces a flaw on the surface of the material 20, after one revolution of that particular roller, the flaw will recur in the same lane with the separation distance of the flaw being determined by the circumference of the roller. Having stored the necessary repeat interval sizes or roller circumference distances in the computer, the separation distance 63 between flaws 62 and 64 is compared with the stored interval sizes to see if a match occurs. If such a match occurs, a post-filter shift register is created in the computer because the matched pair indicates that further processing is desirable. The post-filter section projects the location 65 based on data in the post-filter shift register (within a selected tolerance window) which is measured by the distance 63 from flaw 64 along lane 3 where the next flaw or defect should occur if it repeats. Flaw 66 shown in FIG. 3 represents a defect occurring in projected window 65. With the occurrence of flaw 66 within its proper projected window 65, the post-filter is updated to project the next window 67, which is spaced a distance 63 down lane 3 from the actual location of flaw 66. When a random flaw 68 occurs having missed window 67, a miss is recorded in the post-filter section and a projection of the next window location 69 is computed by adding distance 63 to the center of window 67. Further projection of windows based on an initial match are continued by either the distance from the occurrence of the last flaw within a window or from the center of a projection window in the event of a miss.

Summarizing the above, the pre-filter section has in storage a history of previous defects by lane up to and including the largest repeat size to be detected. New defects entering the pre-filter section of the computer 50 are tested against each previous defect in the pre-filter to determine if any pair (the new defect and any one of the previous defects) make a match, thereby being worthy of further processing. The comparison which is made measures the down-web separation distance against a predetermined list of repeat sizes. If the separation distance between defects matches a repeat size to within a specified tolerance, further processing is warranted, and the pre-filter section creates a post-filter sequence that will be used to examine subsequent expected defect sequence locations. This sequence tester is called the post-filter shift register. The post-filter section contains post-filter shift registers set up by the pre-filter section. New defects are tested against all existing post-filter shift registers in that lane to determine if the new defects belong to an established repeat sequence. If so, the appropriate shift register which has been set up in the post-filter captures that defect and updates the shift register to the newly acquired matrix position specified by the new defect. The condition of three or more out of five sequenced locations containing defects is sufficient for a repeat defect alarm. Such an alarm may be used for the computer to direct the stopping of the rollers 32. With the position information so provided the roller can be examined and the cause of the defect can be cured. The presence of the shift register in the post-filter of the computer is not by itself sufficient to provide an alarm, and such a shift register in accordance with the present invention is eliminated whether or not an alarm has been recognized after three successive locations are found void of defects.

Figure 4:
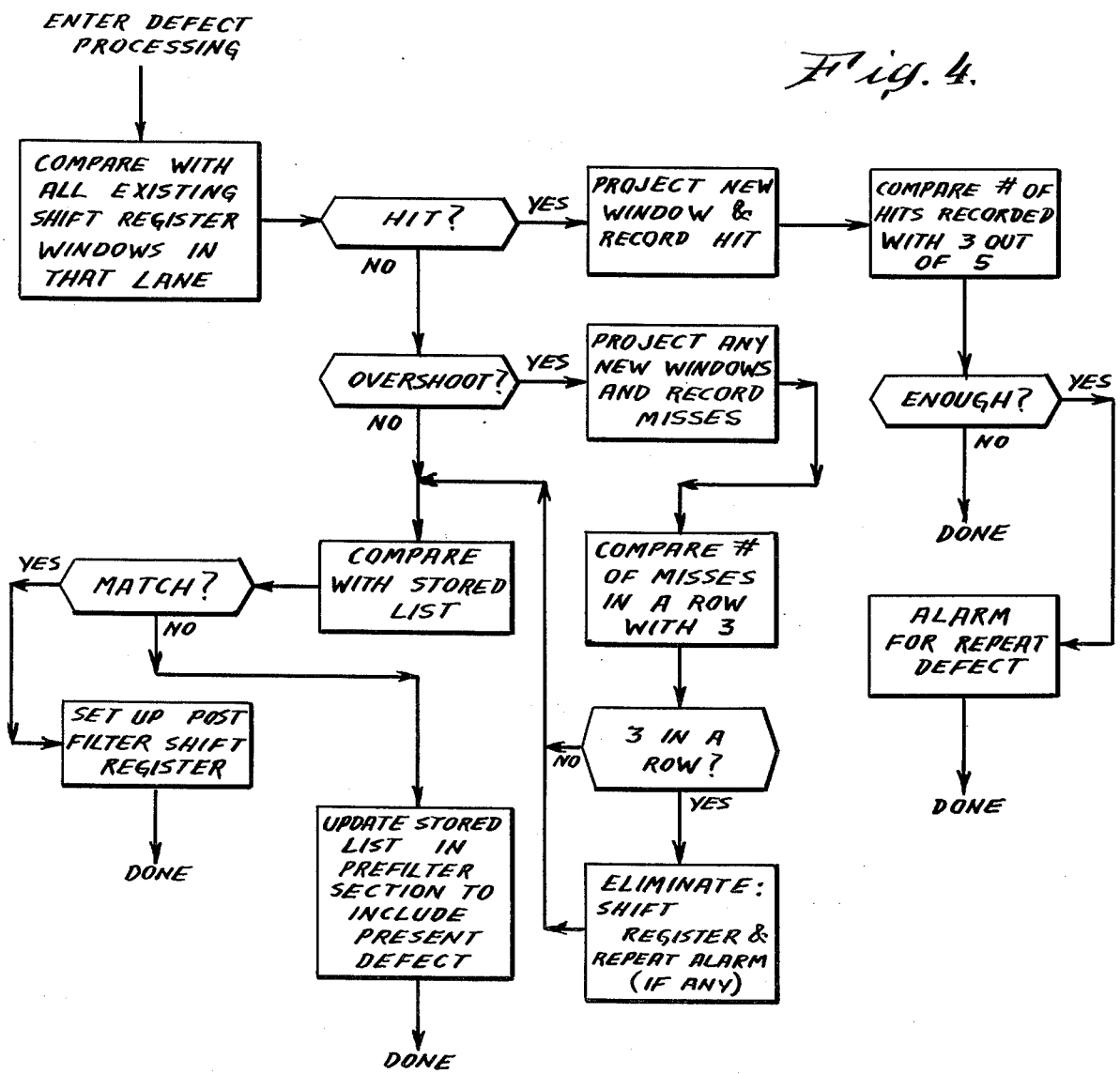
FIG. 4 is a flow diagram for one pass of defect processing, illustrating the processing technique carried out by the systems shown in FIGS. 1 and 2.

This processing is illustrated in the flow diagram shown in FIG. 4. Defects from the flaw discriminator 28 are entered into the computer 50, and first compared with any and all existing shift register windows which have previously been established in that lane. If the defect so entered occurs within an existing window in the post-filter section of the computer 50, a "hit" occurs, which produces a projection of a new window and a hit is recorded. The recorded hit is then compared to see if three out of five hits have been recorded or occurred, and if enough hits to produce the three out of five comparison have been made, an alarm is provided to indicate a repeat defect. If a sufficient number of hits have not occurred, the recorded hit is simply stored for the next comparison.

If a hit does not occur on the comparison with existing windows in that lane and an overshoot occurs, in other words, the new flaw occurs beyond an existing window, then a new window is projected from the center of the missed window, and a "miss" is recorded. The recorded miss is then compared to see if three misses in a row have occurred. If three misses in a row have occurred, the register containing the history of this particular series of flaws is eliminated. Whether three misses occur in a row or not, the overshoot flaw is then compared with the stored list of sizes which, if a match occurs, sets up a new post-filter shift register which can be tested with new flaws as they occur. If no match occurs, the history in the pre-filter section is updated to include the new defect.

If a flaw is entered and on being compared with all existing windows provides no hit and does not occur as an overshoot, but in effect occurs prior to a given window, than that flaw is compared with the stored list to see if a match occurs, and a post-filter shift register is set up for that flaw. If no match occurs, the history of the pre-filter section is updated to include the new defect.

The repeat defect system disclosed above is optimized for minimum processing of random data. High data rates confined to a lane such as would be caused by a streak on the material cause automatic data lockout until the high data rate ceases. The repeat defect processing also makes use of data processing time only in the presence of defects except in the absence of new defects to stimulate processing in that lane and a predetermined advancement of the web (e.g. one foot); in such a case, all of the post-filter shift registers are updated and tested after three successive voids. The system provides maximum information with a minimum of processing time. The advantages of the repeat defect detection system provide precise location information on a two-coordinate basis, which allows the correction of a problem creating the defects with a minimum of down time for the entire system.

Since other modifications, varied to fit particular operating requirements and environments, will be apparent to those skilled in the art, the invention is not considered limited to the examples chosen for purposes of disclosure, and covers all changes and modifications which do not constitute departures from the true spirit and scope of this invention.

What is claimed is:

1. A repeat defect detection system for detecting repetitive flaws on predetermined areas of moving web of material being examined, comprising in combination
   (a) a source of radiation,
   (b) scanning means for scanning said source of radiation in a predetermined scan path over the web of material being examined,
   (c) detector means positioned for receiving radiation applied by said source from the material being examined and generating signals in response to the intensity of radiation applied thereto,
   (d) flaw discriminator means coupled to said detector means for passing flaw signals of predetermined characteristics in accordance with the requirements of said discriminator means,
   (e) lane means for dividing the web of material being examined into predetermined lane areas along the length of travel of the web and means for generating lane signals representing said lane areas for flaw signal processing purposes, and
   (f) settable recirculating processing means coupled to said flaw discriminator means and said lane signals for providing flaw signal matrix coordinator outputs indicative of lane number versus downweb position of each new flaw passed by said discriminator means, said processing means having means for locking out individual lanes with a predetermined high data rate until such predetermined high data rate disappears for a predetermined time interval.

2. The repeat defect flaw detection system set forth in claim 1 including
   (a) means for determining separation distances between a next succeeding flaw signal and a prior flaw signal in a given lane,
   (b) means for comparing said separation distances in any given lane with a predetermined list of separation distances for providing matched pairs of flaws,
   (c) means for projecting future flaw locations in a given lane band from matched pairs of flaw separations,
   (d) means for comparing any new flaw in a given lane with said future flaw locations, and
   (e) means for generating an alarm indication of flaw size and lane location on a predetermined number of flaw repeats in a given lane which coincide with projections of said future flaw locations.

3. The repeat defect flaw detection system set forth in claim 2, including means for resetting a given lane by removing flaw data for a given flaw on a predetermined number of misses in a row in a comparison with projections of said future flaw locations for that flaw.

4. The method of providing flaw information in accordance with the position of flaws occurring in a moving web of material being examined by a flaw detection system in which a source of radiation is scanned on a surface of the moving web of material for locating flaws thereon comprising the steps of
   (a) dividing said moving web of material into lanes and generating lane signals in accordance with the position of the scan across said material,
   (b) sorting the flaw signals in accordance with the lane in which they occur,
   (c) quantizing the number of flaws in a given lane and disabling a given lane for predetermined high flaw rates in that lane until the high flaw rate subsides for a predetermined interval of travel of said moving web of material, and
   (d) providing down-web and cross-web position data for all flaws occurring on the material for all non-disabled lanes.

5. The method set forth in claim 4 for providing repeat flaw indications including steps of
   (a) determining separation distances between a next succeeding flaw and prior flaws in a given lane,
   (b) comparing said separation distances to a predetermined list of sizes,
   (c) projecting future flaw locations when match is produced on said comparisons,
   (d) testing each new defect in a given lane for coincidence with said projected future locations,
   (e) generating a hit or miss list based on said testing step, and
   (f) indicating the lane and size of a repeat flaw after a predetermined number of hits.

6. The method set forth in claim 5 including the step of resetting those lanes by removing all previous flaw data accumulation with respect to a particular flaw on the occurrence of a predetermined number of misses for that flaw in a given lane.

7. The structure set forth in claim 1 wherein said settable recirculating processing means includes a read only memory and a recirculating memory, said recirculating memory being coupled between the input and output of said read only memory.

* * * * *